United States Patent
Zorn et al.

(10) Patent No.: US 12,139,447 B2
(45) Date of Patent: Nov. 12, 2024

(54) METHOD FOR DIISOCYANATE RECOVERY FROM DISTILLATION RESIDUES WITH BITUMEN

(71) Applicant: Covestro Deutschland AG, Leverkusen (DE)

(72) Inventors: Anna-Marie Zorn, Ettlingen (DE); Thomas Guttmann, Langenfeld (DE); Claudine Stoye, Cologne (DE); Sascha Tadjbach, Bergisch Gladbach (DE); Thomas Voigt, Langenfeld (DE); Irene Cristina Latorre Martinez, Leverkusen (DE); Joerg Morawski, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 727 days.

(21) Appl. No.: 17/260,624

(22) PCT Filed: Jul. 15, 2019

(86) PCT No.: PCT/EP2019/068938
§ 371 (c)(1),
(2) Date: Jan. 15, 2021

(87) PCT Pub. No.: WO2020/016142
PCT Pub. Date: Jan. 23, 2020

(65) Prior Publication Data
US 2021/0276944 A1 Sep. 9, 2021

(30) Foreign Application Priority Data
Jul. 18, 2018 (EP) ..................... 18184144

(51) Int. Cl.
C07C 263/20 (2006.01)
B01D 1/06 (2006.01)
B01D 1/22 (2006.01)
B01D 3/34 (2006.01)
C07C 263/10 (2006.01)
C08G 18/42 (2006.01)
C08G 18/76 (2006.01)

(52) U.S. Cl.
CPC ............ *C07C 263/20* (2013.01); *B01D 1/065* (2013.01); *B01D 1/22* (2013.01); *B01D 3/34* (2013.01); *C07C 263/10* (2013.01); *C08G 18/4238* (2013.01); *C08G 18/7678* (2013.01); *C07C 2601/16* (2017.05); *C07C 2602/10* (2017.05)

(58) Field of Classification Search
CPC .. B01D 1/065; B01D 1/22; B01D 3/34; C07C 263/10; C07C 263/20; C07C 2602/10; C07C 2601/16; C08G 18/4238; C08G 18/7678
See application file for complete search history.

(56) References Cited

U.S. PATENT DOCUMENTS

| | | | |
|---|---|---|---|
| 3,694,323 A | 9/1972 | Cooper et al. | |
| 3,987,075 A * | 10/1976 | Schnabel | C07C 263/20 203/43 |
| 4,118,286 A * | 10/1978 | Burns | C07C 263/20 203/69 |
| 4,293,680 A | 10/1981 | Mazanek et al. | |
| 5,354,432 A * | 10/1994 | Arribas | C07C 263/10 528/902 |
| 5,446,196 A * | 8/1995 | Benedix | C07C 263/20 560/352 |
| 5,606,005 A * | 2/1997 | Oshita | C08G 18/4238 528/906 |
| 5,609,735 A * | 3/1997 | Hetzel | C07C 263/20 203/52 |
| 7,358,388 B2 * | 4/2008 | Woelfert | C07C 263/20 560/352 |
| 7,524,405 B2 * | 4/2009 | Sohn | C07C 263/20 203/80 |

(Continued)

FOREIGN PATENT DOCUMENTS

| | | |
|---|---|---|
| GB | 1083910 A | 9/1967 |
| GB | 1336385 A | 11/1973 |
| WO | 2018134238 A1 | 7/2018 |

OTHER PUBLICATIONS

International Search Report, PCT/EP2019/068938, date of mailing: Oct. 9, 2019, Authorized officer: Irmgard Seitner.
Ullmanns Encyklopadie der technischen Chemie [Ullmann's Encyclopedia of Industrial Chemistry], 4th edition, vol. 13, pp. 347-357, Verlag Chemie, GmbH, D-6940 Weinheim, 1977.
Ullmanns Encyclopedia of Industrial Chemistry, Wiley-VCH Verlag Gmbh & Co KGaA, Weinheim, Online ISBN: 9783527306732, DOI: 10.1002/14356007.a14_611, p. 63 ff (2012).

(Continued)

*Primary Examiner* — Jonathan Miller
(74) *Attorney, Agent, or Firm* — The Webb Law Firm

(57) ABSTRACT

The invention relates to a method for recovering a diisocyanate which is solid at room temperature from a distillation residue from a process for producing the diisocyanate, comprising the following steps: (i) mixing the distillation residue with a bitumen such that a mixture is obtained which contains 70 to 90 wt % of the distillation residue and 10 to 30 wt % of the bitumen, each in relation to the mixture, (ii) distilling the mixture in a thin-film evaporator or a falling film evaporator to obtain a sump discharge and a gaseous product stream, (iii) condensing the gaseous product stream and obtaining a solid containing the diisocyanate which is solid at room temperature. The invention further relates to the use of a thin-film evaporator or falling film evaporator, to a composition containing the diisocyanate which is solid at room temperature, and to a method for producing an elastomer from this composition and to the elastomer itself.

8 Claims, No Drawings

(56) References Cited

U.S. PATENT DOCUMENTS

| | | | |
|---|---|---|---|
| 8,088,944 B2 * | 1/2012 | Woelfert | C07C 263/10 |
| | | | 560/352 |
| 9,029,595 B1 | 5/2015 | Steffens et al. | |
| 9,061,971 B2 * | 6/2015 | Wolfert | C07C 263/20 |
| 9,272,988 B2 | 3/2016 | Laue et al. | |

OTHER PUBLICATIONS

D. J. Prepelka and J.L. Wharton in Journal of Cellular Plastics, Mar./Apr. 1975, pp. 87 to 98.
U. Knipp in Journal of Cellular Plastics, Mar./Apr. 1973, pp. 76-84.

* cited by examiner

METHOD FOR DIISOCYANATE RECOVERY FROM DISTILLATION RESIDUES WITH BITUMEN

CROSS REFERENCE TO RELATED APPLICATIONS

This application is a national stage application under 35 U.S.C. § 371 of PCT/EP2019/068938, filed Jul. 15, 2019, which claims benefit of European Application No. 18184144.6, filed Jul. 18, 2018, both of which are incorporated herein by reference in their entireties.

FIELD OF THE INVENTION

The present invention relates to a method of separating a room temperature solid diisocyanate from a distillation residue that arises in a process for preparing the diisocyanate. The invention further provides the room temperature solid diisocyanate obtainable by this method. In addition, the invention further provides for the use of a thin-film evaporator or falling-film evaporator, a composition comprising the room temperature solid diisocyanate, and a method of producing an elastomer from this composition and the elastomer itself.

BACKGROUND OF THE INVENTION

The industrial scale preparation of diisocyanates by reacting amines with phosgene in solvents is known and described in detail in the literature (Ullmanns Encyklopädie der technischen Chemie [Ullmann's Encyclopedia of Industrial Chemistry], 4th edition, volume 13, pages 347-357, Verlag Chemie, GmbH, D-6940 Weinheim, 1977 or else EP 1 575 908 A1). The purification of the diisocyanates prepared by these methods by distillation processes affords a distillation residue. Depending on the chemical nature of the diisocyanate prepared, this residue contains a considerable proportion of monomeric diisocyanate. This residue can be disposed of by incineration, but in that case the monomeric diisocyanate present therein is also lost.

Therefore, various methods have been developed for separating and recovering the monomeric diisocyanate present in the residue from the distillation residue. For this purpose, the residues are mixed with high-boiling hydrocarbons, for example bitumen, and then the diisocyanate present in the residue is separated in a kneader-drier, paddle drier or batchwise distillation method.

If the residue has a high viscosity extending as far as the solid state and the monomeric diisocyanates are not liquid at room temperature, the viscosity of the residue has to be lowered prior to any recovery in order to be able to perform a separation method at all. Heating of non-liquid residues does lower their viscosity, but there are also unwanted side reactions—for example oligomerizations—of the diisocyanate to be isolated. A further challenge in the recovery is that, in distillative methods, the bottoms output, i.e. the portion that remains from the diisocyanate separated, can also have a high viscosity and can therefore be removed from the separation apparatus only with difficulty. In conventional recovery methods, this high viscosity frequently results from oligomerizations of diisocyanate still present in the bottoms output that have been caused by high temperatures.

Naphthalene diisocyanate (NDI) has found broad industrial use and can be prepared by known methods described at the outset, for example phosgenation, from naphthalene-diamine (NDA). Since monomeric naphthalene diisocyanate is a solid, the purification of the product fundamentally constitutes a challenge compared to other isocyanates that are liquid at processing temperature, for example tolylene diisocyanate (TDI). The difficulties are increased by the physical properties of naphthalene diisocyanate because it melts at 127° C. and already begins to sublime at 130° C. The residue from the process for purifying naphthalene diisocyanate still contains about 70-80% by weight of monomeric naphthalene diisocyanate. 150 to 300 tonnes per year of naphthalene diisocyanate present in the residue from the purification method are incinerated. The recovery of monomeric naphthalene diisocyanate in a batchwise distillation method recovers about 50% of the monomeric naphthalene diisocyanate present in the residue. Typically, the residue in this method is dissolved in about 30% by weight of bitumen.

EP 0 626 368 A1 describes a method of preparing pure distilled isocyanates in which the residue is admixed with 2% to 50% by weight of high-boiling hydrocarbons and the isocyanate is extracted from this residue at temperatures of 160° C. to 280° C. In one working example, residue containing the room temperature liquid tolylene diisocyanate is admixed with 12% by weight of bitumen B80, corresponding to bitumen 70/100 under the new designation, and introduced into a kneader-drier heated to 240° C. Kneader-driers are used in this method, which mean relatively complex technology with mechanically moving parts. Moreover, it has to be ensured in this method that free-flowing material is discharged continuously from the kneader-drier, and so the application of the method is not suitable for all kinds of residues. The publication does also refer to naphthalene diisocyanate, but only discloses tolylene diisocyanate in the experimental. There is no discussion of the particular difficulties of recovering a room temperature solid diisocyanate.

EP 2 872 481 discloses a spray-drying method for the purification of distillation residues that are obtained in the preparation of isocyanate. This involves spraying the residue into a reactor together with a carrier gas such as nitrogen, noble gases or carbon dioxide, and separating off monomeric diisocyanate. However, this method is performable only when the temperature of the distillation residue is sufficiently high that the viscosity of the residue is sufficiently low for it to be sprayed in. The document discloses temperatures of the residue of 20 to 300° C. The sole working example relates to tolylene diisocyanate, which is liquid at room temperature. There is no discussion of the particular difficulties of recovering a room temperature solid diisocyanate.

U.S. Pat. No. 3,694,323 discloses a method of recovering an isocyanate from a residue with the aid of a further isocyanate which has a higher boiling point than the isocyanate to be purified and hence lowers the viscosity of the residue and enables purification. However, a disadvantage of this method is that the method has a comparatively high energy requirement since temperatures between 190° C. and 250° C. are required in the examples for the purification of TDI. The document also refers generally to naphthalene diisocyanate, but discloses only tolylene diisocyanate in the experimental and does not contain any teaching as to the particular difficulties in the recovery of a room temperature solid diisocyanate.

WO 2007/036479 A1 also relates to distillation residues that are not liquid and discloses a method of recovering an isocyanate in which the residue, over the entire dwell time in the apparatus for recovery, at a temperature of 210 to 330° C. and a pressure below 300 hPa, forms a high-viscosity liquid and/or a non-brittle solid, and is discharged from this apparatus by a means of forced conveying of non-solid media. The document does not refer to use of in the auxiliaries or additives.

DE 2035773 discloses a recovery method in which the diisocyanate is recovered from the residue with the aid of a drop-tube evaporator. The temperature at which the method is conducted is up to 250° C. The experimental discloses a performance temperature of 189° C. and a pressure of 9 hPa.

Application EP 17151971.3 EP describes a method of recovering an isocyanate from its phosgenation residue using ≥32% by weight of bitumen as solvent.

A disadvantage of the conventional methods of recovering diisocyanate from the distillation residue is the use of relatively large amounts of an additive that can contaminate the recovered diisocyanate. Furthermore, methods in which kneader-driers or paddle driers are used are characterized by high capital costs and maintenance expenditure. In addition, the performance of most conventional methods at high temperatures of more than 180° C. requires a large amount of energy. Moreover, these temperatures lead to unwanted oligomerization reactions of the monomeric diisocyanate. A disadvantage of the known batchwise distillation methods is that they are not continuous processes.

There is therefore a need for a method for the recovery of diisocyanates, especially of room temperature solid diisocyanates such as naphthalene diisocyanate, from distillation residues that are obtained in the preparation of diisocyanates, in which a at least the same or a higher proportion of the diisocyanate present in the residue can be recovered than in conventional methods, and which simultaneously consumes a lower level of energy and additives. Additionally advantageous are methods that can be performed as a continuous process. In addition, the diisocyanate recovered was to be very substantially free of extraneous materials, for example additives from the recovery process.

DETAILED DESCRIPTION OF THE INVENTION

It was therefore an object of the present invention to provide a method of recovering room temperature solid diisocyanates, especially naphthalene diisocyanate, from a distillation residue, by which at least an equal or even a higher proportion of the diisocyanate present in the residue, especially of naphthalene diisocyanate, can be recovered than by conventional methods. At the same time, the method of the invention is to consume less energy and a lower level of additives than conventional methods. Furthermore, the diisocyanate recovered is to be very substantially free of extraneous materials, for example additives from the recovery process, such that it can be used without further purification processes as reactant for further syntheses, for example polymer syntheses.

This object was achieved by a method of separating a room temperature solid diisocyanate from a distillation residue from a method for preparing the diisocyanate, comprising the following steps:
(i) mixing the distillation residue with a bitumen in such a way as to obtain a mixture containing 70% to 90% by weight of the distillation residue and 10% to 30% by weight of the bitumen, based in each case on the mixture,
(ii) distilling the mixture in a thin-film evaporator or a falling-film evaporator to obtain a bottoms output and a gaseous product stream,
(iii) condensing the gaseous product stream to obtain a solid material comprising the room temperature solid diisocyanate.

It has now been found that, surprisingly, even room temperature solid diisocyanates can be recovered from a distillation residue with comparatively small amounts of a bitumen in a thin-film evaporator and/or falling-film evaporator, wherein at least an equal or even a higher proportion of diisocyanate is recovered than in comparable methods. In spite of a smaller proportion of bitumen compared to conventional methods, it is additionally possible to keep the mixture of the residue with the bitumen liquid throughout the distillation process. Furthermore, the recovered diisocyanate has a very low level of impurities.

In the present context, "room temperature solid diisocyanates" is understood to mean that the diisocyanates are in the solid state of matter at 23° C. and standard pressure.

In the present context, naphthalene diisocyanate is understood as an umbrella term for the possible isomers or mixtures thereof. Examples of such isomers are naphthalene 1,5-diisocyanate or naphthalene 1,8-diisocyanate.

Suitable thin-film evaporators are, for example, star blade rotor thin-film evaporators or wiper-blade thin-film evaporators or short-path evaporators.

Suitable falling-film evaporators are, for example, shell and tube downpipe evaporators or helical tube evaporators.

Bitumen, especially the different sulfur content of various bitumens and the production of bitumen, are known to the person skilled in the art. The bitumen in the mixture from step (i) preferably has a sulfur content of 2.5% to 3.1% by weight, more preferably 2.7% to 3.1% by weight, especially preferably from 2.9% to 3.08% by weight, based in each case on the bitumen. In a preferred embodiment, the bitumen in the mixture from step (i) is bitumen 160/220 from Shell.

The distillation residue in step (i) preferably contains from 30% to 70% by weight of the room temperature solid diisocyanate, more preferably 40% to 60% by weight, especially preferably 45% to 50% by weight, based in each case on the distillation residue.

Preferably, in step (i), 85% to 70% by weight of the distillation residue is mixed with from 15% to 30% by weight of the bitumen, based in each case on the sum total of the masses of the distillation residue and the bitumen. This gives rise to the additional advantage that the yield of room temperature solid diisocyanate recovered can be further increased and the mixture is kept in liquid form throughout the distillation process.

In a further preferred embodiment, the room temperature solid diisocyanate is naphthalene 1,5-diisocyanate, naphthalene 1,8-diisocyanate, phenylene 1,4-diisocyanate, tetralin diisocyanate, o-toluidine diisocyanate, durene diisocyanate, benzidine diisocyanate and/or anthrylene 1,4-diisocyanate, more preferably naphthalene 1,5-diisocyanate, naphthalene 1,8-diisocyanate, phenylene 1,4-diisocyanate, tetralin diisocyanate and/or o-toluidine diisocyanate and more preferably naphthalene 1,5-diisocyanate and/or naphthalene 1,8-diisocyanate.

In principle, the room temperature solid diisocyanates can be prepared by any routes, for example by reaction of the corresponding diamines or salts thereof with phosgene. All that is important in each case is that the method utilized leaves at least one distillation residue containing room temperature solid diisocyanates that can then be used in step (i) of the invention.

It is particularly preferable that the method for preparing the diisocyanate is a phosgenation of a diamine, more preferably a liquid phase phosgenation of a diamine.

Preferably, in the process for preparation of the diisocyanate, a diamine that has the structure of the diisocyanate apart from the isocyanate groups is used, but in which the two amino groups have been exchanged for isocyanate groups in the preparation process. By way of example, naphthalene 1,5-diamine is the corresponding diamine of naphthalene 1,5-diisocyanate. When the room temperature solid diisocyanate is an isomer mixture, a corresponding isomer mixture of diamines is used.

The continuous preparation of organic isocyanates by reaction of primary organic amines with phosgene has been described many times and is performed on the industrial scale (see, for example, Ullmanns Encyclopedia of Industrial Chemistry, Wiley-VCH Verlag Gmbh & Co KGaA, Weinheim, Online ISBN: 9783527306732, DOI: 10.1002/14356007.a14_611, p. 63 ff (2012)). Particular preference is given to preparing the room temperature solid diisocyanate from the corresponding diamine using phosgene by the method known from WO 2014/044699 A1, which comprises the following steps:

(A) preparing a suspension of the corresponding diamine in an inert solvent, where the diamine is distributed in the solvent by means of a dynamic mixing unit, (B) phosgenating the diamine suspended in the inert solvent to obtain the respective diisocyanate, wherein the dynamic mixing unit in step (A) is selected from the group consisting of dispersing disks and rotor-stator systems, preferably rotor-stator systems, more preferably colloid mills, toothed dispersing machines and three-roll mills. Very particular preference is given to toothed dispersing machines as dynamic mixing units.

The dispersing disks and rotor-stator systems mentioned in the above paragraph have the same meaning as disclosed at page 4 line 17 to page 5 line 11 of WO 2014/044699 A1 5.

Suitable inert solvents are aromatic solvents, which may also be halogenated. Examples of these are toluene, monochlorobenzene, o-, m- or p-dichlorobenzene, trichlorobenzene, chlorotoluenes, chloroxylenes, chloroethylbenzene, chloronaphthalenes, chlorodiphenyls, xylenes, decahydronaphthalene, benzene or mixtures of the above solvents. Further examples 10 of suitable organic solvents are methylene chloride, perchloroethylene, hexane, diethyl isophthalate, tetrahydrofuran (THF), dioxane, trichlorofluoromethane, butyl acetate and dimethylformamide (DMF). Preference is given to using monochlorobenzene or o-dichlorobenzene or a mixture of the two; particular preference is given to using monochlorobenzene.

Phosgene is used in excess in the reaction in step (B). This means that more than one mole of phosgene is used per mole of amine groups. The molar ratio of phosgene to amine groups is accordingly from 1.01:1 to 20:1, preferably 1.1:1 to 10:1, more preferably 1.1:1 to 5.0:1. If necessary, further phosgene or phosgene solution can be supplied to the reaction mixture during the reaction in order to maintain a sufficient excess of phosgene or to compensate for loss of phosgene.

The reaction can be performed continuously and batchwise. Useful reactors include stirred tanks, tubular reactors, spray towers or else loop reactors. In principle, it is alternatively possible to utilize other designs that are not listed here by way of example. Preference is given to batchwise operation.

The reaction can be conducted until complete conversion to the isocyanate within the first reaction stage. Alternatively, it may be advantageous or necessary to conduct a partial conversion, especially of residues of amine hydrochloride, in a downstream reactor. The downstream reactor may comprise customary reactor designs with different degrees of backmixing, such as stirred tanks, loop reactors or tubular reactors. It may also be advantageous to divide the reaction mixture into substreams according to its particle size distribution and feed them separately to one or more downstream reactors. Useful designs for the removal include known apparatuses such as filters, cyclones or gravitational separators, for example. The substreams may be treated before or during the reaction by appropriate mechanical methods of adjusting the particle size, for example by grinding.

The unconverted phosgene is usually recycled, optionally after purification, and reused for phosgenation.

Methods available for separating the diisocyanate from the solvent include those known to the person skilled in the art, for example crystallization, sublimation or distillation, optionally with addition of seed crystals or azeotroping agents, for example. Preference is given to using a method comprising crystallization or distillation. The abovementioned methods leave a highly viscous or even solid residue that contains a variably high proportion of diisocyanates. It is possible with preference to use residues from the methods of crystallization and sublimation as distillation residue for the method of the invention.

In a further preferred embodiment, the residue used in the method of the invention contains ≥0% by weight to ≤4% by weight, preferably ≥0.001% by weight to ≤2% by weight and more preferably ≥0.01% by weight to ≤1% by weight, based in each case on the total amount of the residue containing room temperature solid diisocyanates, of monomeric diisocyanates that have a boiling temperature above the boiling temperature of the room temperature solid diisocyanate and are different therefrom. This is particularly advantageous since, even without this addition, a high yield can be achieved in the recovery and the purified room temperature solid diisocyanate thus remains very substantially free of these impurities.

The percentages by weight of monomeric diisocyanates having a boiling temperature above the boiling temperature of the room temperature solid diisocyanate are determined by gas chromatography by means of an FID detector, preferably using an Optima 5 column and the following parameters: split rate: 8.31:1 mL/min; flow rate: 96.4 mL/min; pressure: 0.7 bar, carrier gas: helium, injection volume: 1 µL, inliner: straight split liner filled with Carbofritt, equating the area percentage with the percentage by weight in the evaluation.

In a further preferred embodiment, the residue has an average residence time in the treatment in step (ii) of ≥1 to ≤15 minutes, preferably of ≥1 to ≤10 minutes and more preferably of ≥1 to ≤5 minutes in the at least one thin-film evaporator and/or falling-film evaporator; more preferably, the residue has this residence time in a conventional glass falling-film evaporator having an evaporator area of 0.1 m$^2$ (diameter 100 mm, length 300 mm). This results in the advantage that the likelihood of unwanted side reactions—for example oligomerizations—can be reduced further.

Step (ii) of the method is preferably performed at a temperature of 130° C. to 160° C. and a pressure of 0.4 to 4 mbar, more preferably from 140° C. to 160° C. and from 0.6 mbar to 2 mbar, especially preferably from 150° C. to 160° C. and from 0.7 to 1.5 mbar. This gives rise to the advantage that the formation of by-products, i.e. oligomerization of the diisocyanate during the distillation, can be very substantially suppressed.

Preferably, the bottoms output from step (ii) is not in solid form at the prevailing temperature at the outlet from the thin-film evaporator or falling-film evaporator. Preferably, the bottoms output is discharged continuously from the distillation apparatus and then either recycled, for example by incineration to obtain heat, or discarded. More preferably, the bottoms output is liquid under the distillation conditions.

In a further preferred embodiment, a coolant is used in the distillation in step (iii), wherein the coolant temperature is preferably below the melting point of the room temperature solid diisocyanate. The coolant serves for rapid condensation of the product stream.

The solid material from step (iii) preferably contains at least 95% by weight of the room temperature solid diisocyanate, more preferably at least 97% by weight, especially preferably at least 99% by weight, based in each case on the solid material. Preferably, the proportion of solid diisocyanate in the solid material is determined by gas chromatography methods. The reduced use of auxiliaries such as bitumen in step (i) of the method minimizes the contamination of the monomeric room temperature solid diisocyanate obtained from the residue.

Preferably, the method recovers ≥60% by weight, preferably ≥70% by weight and most preferably ≥80% by weight of the room temperature solid diisocyanates that are still present in the residue in step (i).

A further embodiment of the invention relates to the use of a mixture containing 70% to 90% by weight of a distillation residue from a method for preparing a room temperature solid diisocyanate and 10% to 30% by weight of a bitumen, based in each case on the mixture, in a method of separating the diisocyanate by distillation by means of a thin-film evaporator or falling-film evaporator.

Preferably, the solid material containing the room temperature solid diisocyanate from step (iii) of the method, alone or else in mixtures with a diisocyanate obtained directly from the first purification stage after the phosgenation reaction, can be sent to all end uses familiar to the person skilled in the art. In one embodiment who for production of high-performance elastomers, for example Vulkollan®, are used. Especially preferred is the further processing of the solid material with NCO-reactive compounds such as polyols to give polyurethanes, optionally via prepolymers as intermediates.

A further embodiment of the invention relates to a composition comprising a solid material comprising a room temperature solid diisocyanate from step (iii) of a method as described herein and at least one NCO-reactive compound, preferably at least one polyester polyol.

The present invention further provides a method of producing an elastomer, in which at least one composition of the invention is chemically reacted, optionally while heating, and the elastomer produced or producible by this method.

These elastomers are preferably polyurethanes that are optionally obtained via prepolymers as intermediates.

These polyurethanes preferably have apparent densities of 200 kg/m³ to 1400 kg/m³, more preferably of 600 kg/m³ to 1400 kg/m³ and most preferably of 800 kg/m³ to 1400 kg/m³. Very particular preference is given to producing cellular or bulk cast elastomers, more preferably polyester polyol-based cast elastomers.

The above-described composition may preferably comprise customary auxiliaries and additives, for example rheology improvers (for example ethylene carbonate, propylene carbonate, dibasic esters, citric esters), stabilizers (for example Brønsted and Lewis acids, for instance hydrochloric acid, phosphoric acid, benzoyl chloride, organo mineral acids such as dibutyl phosphate, and also adipic acid, malic acid, succinic acid, pyruvic acid or citric acid), UV stabilizers (for example 2,6-dibutyl-4-methylphenol), hydrolysis stabilizers (for example sterically hindered carbodiimides), emulsifiers and catalysts (for example trialkylamines, diazabicyclooctane, tin dioctoate, dibutyltin dilaurate, N-alkylmorpholine, lead octoate, zinc octoate, tin octoate, calcium octoate, magnesium octoate, the corresponding naphthenates and p-nitrophenoxide and/or else mercury phenylneodecanoate) and fillers (for example chalk), dyes which may be incorporable into the polyurethane/polyurea to be formed at a later stage (which thus possess Zerewitinoff-active hydrogen atoms) and/or color pigments.

NCO-reactive compounds used may be any compounds known to those skilled in the art.

Preferred NCO-reactive compounds are polyether polyols, polyester polyols, polycarbonate polyols and polyether amines having an average OH or NH functionality of at least 1.5, and short-chain polyols and polyamines (chain extenders or crosslinkers), as are sufficiently well known from the prior art. These may be, for example, low molecular weight diols (e.g. ethane-1,2-diol, propane-1,3- or -1,2-diol, butane-1,4-diol), triols (e.g. glycerol, trimethylolpropane) and tetraols (e.g. pentaerythritol), but also higher molecular weight polyhydroxyl compounds such as polyether polyols, polyester polyols, polycarbonate polyols, polysiloxane polyols, polyamines and polyether polyamines and polybutadiene polyols.

Polyether polyols are obtainable in a manner known per se by alkoxylation of suitable starter molecules under base catalysis or by the use of double metal cyanide compounds (DMC compounds). Examples of suitable starter molecules for the preparation of polyether polyols are simple low molecular weight polyols, water, organic polyamines having at least two N—H bonds, or any mixtures of such starter molecules. Preferred starter molecules for preparation of polyether polyols by alkoxylation, especially by the DMC method, are especially simple polyols such as ethylene glycol, propylene 1,3-glycol and butane-1,4-diol, hexane-1,6-diol, neopentyl glycol, 2-ethylhexane-1,3-diol, glycerol, trimethylolpropane, pentaerythritol, and low molecular weight hydroxyl-containing esters of such polyols 5 with dicarboxylic acids of the kind specified hereinafter by way of example, or low molecular weight ethoxylation or propoxylation products of such simple polyols, or any desired mixtures of such modified or unmodified alcohols. Alkylene oxides suitable for the alkoxylation are especially ethylene oxide and/or propylene oxide, which can be used in the alkoxylation in any sequence or else in a mixture.

Polyester polyols can prepare in a known manner by polycondensation of low molecular weight polycarboxylic acid derivatives, for example succinic acid, adipic acid, suberic acid, azelaic acid, sebacic acid, dodecanedioic acid, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimer fatty acid, trimer fatty acid, phthalic acid, phthalic anhydride, isophthalic acid, terephthalic acid, citric acid or trimellitic acid, with low molecular weight polyols, for example ethylene glycol, diethylene glycol, neopentyl glycol, hexanediol, butanediol, propylene glycol, glycerol, trimethylolpropane, 1,4-hydroxymethylcyclohexane, 2-methylpropane-1,3-diol, butane-1,2,4-triol, triethylene glycol, tetraethylene glycol, polyethylene glycol, dipropylene glycol, polypropylene glycol, dibutylene glycol and polybutylene glycol, or by ring-opening polymerization of cyclic carboxylic esters such as ε-caprolactone. In addition, it is also possible to polycondense hydroxycarboxylic acid derivatives, for example lactic acid, cinnamic acid or w-hydroxycaproic acid to give polyester polyols. However, it is also possible to use polyester polyols of oleochemical origin. Such polyester polyols can be prepared, for example, by full ring-opening of epoxidized triglycerides of an at least partly olefinically unsaturated fatty acid-containing fat mixture with one or more alcohols having 1 to 12 carbon atoms and subsequent partial transesterification of the triglyceride derivatives to alkyl ester polyols having 1 to 12 carbon atoms in the alkyl radical.

The NCO-reactive compound may contain short-chain polyols or polyamines as crosslinker component or chain extender. Typical chain extenders are diethylenetoluenediamine (DETDA), 4,4'-methylenebis(2,6-diethyl)aniline (MDEA), 4,4'-methylenebis(2,6-diisopropyl)aniline (MDIPA), 4,4'-methylenebis(3-chloro-2,6-diethyl)aniline (MCDEA), dimethylthiotoluenediamine (DMTDA, Ethacure® 300), N,N'-di(sec-butyl)aminobiphenylmethane (DBMDA, Unilink® 4200) or N,N'-di-sec-butyl-p-phenylenediamine (Unilink® 4100), 3,3'-dichloro-4,4'-diaminodiphenylmethane (MBOCA), trimethylene glycol di-p-aminobenzoate (Polacure 740M). Aliphatic aminic chain extenders can likewise be used or used in part. Propane-1,3-diol, butane-1,4-diol, butane-2,3-diol, pentane-1,5-diol, hexane-1,6-diol and HQEE (hydroquinone di(ß-hydroxyethyl) ether), and also water. Very particular preference is given to using butane-1,4-diol for bulk cast elastomers and water for cellular cast elastomers.

An overview of polyurethanes and their properties and uses is given, for example, in the Kunststoffhandbuch [Plastics Handbook], volume 7, Polyurethane [Polyurethanes], 3rd newly revised edition, volume 193, edited by Prof. Dr. G. W. Becker and Prof. Dr. D. Braun (Carl-Hanser-Verlag, Munich, Vienna).

Preference is given to using NCO-terminated prepolymers having an NCO content of 2% to 15% by weight, very particularly of 2-10% by weight. The room temperature solid diisocyanate is preferably reacted with polyols of functionality 2 to 3, preferably 2, and OH number 28-112 mg KOH/g of substance to give prepolymers. Preference is given to using ester-based polyols. The NCO prepolymers thus prepared are either converted further directly or stored as storage-stable prepolymers in drums, for example, until they are ultimately used. Preference is given to using 1,5-NDI-based prepolymers. The production of the cast elastomers (molded articles) is advantageously conducted at an NCO/OH ratio of 0.7 to 1.30. In the case of cellular elastomers, the amount of the mixture introduced into the mold is typically such that the shaped bodies obtained have the density already described. The starting components are typically introduced into the mold at a temperature of 30 to 110° C. The degrees of densification are between 1.1 and 8, preferably between 2 and 6. The cellular elastomers are appropriately produced by a low-pressure technique or especially the reactive injection molding technique (RIM) in open molds, preferably closed molds.

The reactive injection molding technique is described, for example, by H. Piechota and H. Röhr in "Integral Schaumstoffe" [Integral Foams], Carl Hanser-Verlag, Munich, Vienna 1975; D. J. Prepelka and J. L. Wharton in Journal of Cellular Plastics, March/April 1975, pages 87 to 98 and U. Knipp 25 in Journal of Cellular Plastics, March/April 1973, pages 76-84.

Additives such as castor oil or carbodiimides (for example Stabaxols from Rheinchemie as hydrolysis stabilizer, 2,2', 6,6'-tetraisopropyldiphenylcarbodiimide is a known representative) can be added either to the polyol or to the prepolymer. Water, emulsifiers, catalysts and/or auxiliaries and/or additives commonly form the polyol component together with the polyol.

For better demolding, it is customary to provide the molds with external separating agents, for example wax- or silicone-based compounds or aqueous soap solutions. The demolded shaped bodies are typically subjected to subsequent heat treatment at temperatures of 70 to 120° C. for 1 to 48 hours.

Emulsifiers used are, for example, sulfonated fatty acids and further commonly known emulsifiers, for example polyglycol esters of fatty acids, alkylaryl polyglycol ethers, alkoxylates of fatty acids, preferably polyethylene glycol esters, polypropylene glycol esters, polyethylene-polypropylene glycol esters, ethoxylates and/or propoxylates of linoleic acid, 5 linolenic acid, oleic acid, arachidonic acid, more preferably oleic acid ethoxylates. Alternatively, it is also possible to use polysiloxanes. Salts of fatty acids with amines, e.g. diethylamine oleate, diethanolamine stearate, diethanolamine ricinoleate, salts of sulfonic acids, e.g. alkali metal or ammonium salts of dodecylbenzene- or dinaphthylmethanedisulfonic acid, are likewise preferred.

The sulfonated fatty acids can preferably be used as aqueous solutions, for example as a 50% solution. Typical known products are SV and SM additives from Rheinchemie, and WM additive from Rheinchemie as a nonaqueous emulsifier.

The method of producing the cellular PUR cast elastomers is conducted in the presence of water. The water acts both as crosslinker with formation of urea groups and 15 as blowing agent on account of the reaction with isocyanate groups to form carbon dioxide. The amounts of water that can appropriately be used are 0.01% to 5% by weight, preferably 0.3% to 3.0% by weight, based on the weight of the polyol component. The water may be used entirely or partly in the form of the aqueous solutions of the sulfonated fatty acids.

The catalysts may be added individually or else in a blend with one another. These are preferably organometallic compounds such as tin(II) salts of organic carboxylic acids, e.g. tin(II) dioctoate, tin(II) dilaurate, dibutyltin diacetate and dibutyltin dilaurate, and tertiary amines such as tetramethylethylenediamine, N-methylmorpholine, diethylbenzylamine, triethylamine, dimethylcyclohexylamine, diazabicyclooctane, N,N'-dimethylpiperazine, N-methyl-N'-(4-N-dimethylamino)butylpiperazine, N,N,N',N'',N''-pentamethyldiethylenetriamine or the like. Further useful catalysts include: amidines, for example 2,3-dimethyl-3,4,5,6-tetrahydropyrimidine, tris(dialkylaminoalkyl)-s-hexahydrotriazines, especially tris(N,N-dimethylaminopropyl)-s-hexahydrotriazine, tetraalkylammonium hydroxides, for example tetramethylammonium hydroxide, alkali metal hydroxides, 30 for example sodium hydroxide, and alkali metal alkoxides, for example sodium methoxide and potassium isopropoxide, and alkali metal salts of long chain fatty acids having 10 to 20 carbon atoms and optionally pendant OH groups. According to the reactivity to be established, the catalysts are employed in amounts of 0.001% to 0.5% by weight, based on the isocyanate component.

The elastomers of the invention, especially polyurethanes or shaped bodies, differ from the products based on monomeric, room temperature solid diisocyanates known from the prior art, preferably those based on naphthalene 1,5-diisocyanate, in that, by virtue of the method of the invention, the contamination of the monomeric, room temperature solid diisocyanate recovered from the residue with these auxiliaries can also be minimized.

Such cellular PUR cast elastomers, also referred to as shaped bodies, find use as damping elements in vehicle construction, for example in automobile construction, for example as overload springs, buffers, transverse link bearings, rear axle subframe bearings, stabilizer bearings, longitudinal strut bearings, suspension strut bearings, shock absorber bearings, or bearings for wishbones, and also as an emergency wheel on the rim, which has the effect that the vehicle, for example in the event of tire damage, runs on the cellular elastomer and remains controllable. The bulk cast elastomers can also be used as a coating for rolls, wheels and drums, squeegees, screens or hydrocyclones.

The invention relates, in a first embodiment, to a method of separating a room temperature solid diisocyanate from a distillation residue from a method for preparing the diisocyanate, comprising the following steps:
(i) mixing the distillation residue with a bitumen in such a way as to obtain a mixture containing 70% to 90% by weight of the distillation residue and 10% to 30% by weight of the bitumen, based in each case on the mixture,
(ii) distilling the mixture in a thin-film evaporator or a falling-film evaporator to obtain a bottoms output and a gaseous product stream,
(iii) condensing the gaseous product stream to obtain a solid material comprising the room temperature solid diisocyanate.

In a second embodiment, the invention relates to a method according to embodiment 1, characterized in that the bitumen in the mixture from step (i) has a sulfur content of 2.5% to 3.1% by weight, especially 2.7% to 3.1% by weight, preferably from 2.9% to 3.08% by weight, based in each case on the bitumen.

In a third embodiment, the invention relates to a method according to embodiment 1 or 2, characterized in that the distillation residue in step (i) contains from 30% to 70% by weight of the room temperature solid diisocyanate, preferably 40% to 60% by weight, more preferably 45% to 50% by weight, based in each case on the distillation residue.

In a fourth embodiment, the invention relates to a method according to any of embodiments 1 to 3, characterized in that, in step (i), 85% to 70% by weight of the distillation residue is mixed with from 15% to 30% by weight of the bitumen, based in each case on the sum total of the masses of the distillation residue and the bitumen.

In a fifth embodiment, the invention relates to a method according to any of embodiments 1 to 4, characterized in that step (ii) is performed at a temperature of 130° C. to 160° C. and a pressure of 0.4 to 4 mbar, preferably from 140° C. to 160° C. and from 0.6 mbar to 2 mbar, more preferably from 150° C. to 160° C. and from 0.7 to 1.5 mbar.

In a sixth embodiment, the invention relates to a method according to any of embodiments 1 to 5, characterized in that the bottoms output from step (ii) is not in solid form at the prevailing temperature at the outlet from the thin-film evaporator or falling-film evaporator.

In a seventh embodiment, the invention relates to a method according to any of embodiments 1 to 6, characterized in that the solid material from step (iii) contains at least 95% by weight of the room temperature solid diisocyanate, preferably at least 97% by weight, more preferably at least 99% by weight, based in each case on the solid material.

In an eighth embodiment, the invention relates to a method according to any of embodiments 1 to 7, characterized in that the method for preparing the diisocyanate is a phosgenation of a diamine, preferably a liquid phase phosgenation of a diamine.

In a ninth embodiment, the invention relates to a method according to any of embodiments 1 to 8, characterized in that the room temperature solid diisocyanate is naphthalene 1,5-diisocyanate, naphthalene 1,8-diisocyanate, phenylene 1,4-diisocyanate, tetralin diisocyanate, o-toluidine diisocyanate, durene diisocyanate, benzidine diisocyanate and/or anthrylene 1,4-diisocyanate, preferably naphthalene 1,5-diisocyanate, naphthalene 1,8-diisocyanate, phenylene 1,4-diisocyanate, tetralin diisocyanate and/or o-toluidine diisocyanate and more preferably naphthalene 1,5-diisocyanate and/or naphthalene 1,8-diisocyanate.

In a tenth embodiment, the invention relates to the use of a mixture containing 70% to 90% by weight of a distillation residue from a method for preparing a room temperature solid diisocyanate and 10% to 30% by weight of a bitumen, based in each case on the mixture, in a method of separating the diisocyanate by distillation by means of a thin-film evaporator or falling-film evaporator.

In an eleventh embodiment, the invention relates to a composition comprising a solid material comprising a room temperature solid diisocyanate from step (iii) of a method according to any of embodiments 1 to 9 and at least one NCO-reactive compound, preferably at least one polyester polyol.

In a twelfth embodiment, the invention relates to a method of producing an elastomer, in which at least one composition according to embodiment 11 is chemically reacted, optionally while heating.

In a twelfth embodiment, the invention relates to an elastomer produced or producible by a method according to embodiment 12.

The present invention is more particularly elucidated hereinafter with reference to examples and comparative examples, but without restricting it thereto.

EXAMPLES

Monomeric naphthalene diisocyanate (NDI) was separated from distillation residues by various methods. For this purpose, the distillation residue was mixed with various types of bitumen and subjected to a distillation. The following bitumen was used:
Bitumen 70/100 from Shell: 3.5% by weight of sulfur
Bitumen 160/220 from Shell: 2.9% by weight of sulfur
Bitumen with 3.08% by weight of sulfur, mixture of bitumen 70/100 and 160/220
Bitumen with 3.23% by weight of sulfur, mixture of bitumen 70/100 and 160/220

The sulfur content was determined by sulfur elemental analysis after automatic pipe incineration at 1150° C. with addition of oxygen. This is followed by detection with an IR detector as $SO_2$.

The purity of the NDI was determined by gas chromatography. The measurements were effected using a Hewlett Packard HP 6890 with an FID detector and HP-Chemstation software using 5 an Optima 5 column and the following parameters: split rate: 8.31:1 mL/min; flow rate: 96.4 mL/min; pressure: 0.7 bar, carrier gas: helium, injection volume: 1 µL, inliner: straight split liner filled with Carbofritt.

The NDI residues before and after distillation were analyzed by means of GPC to DIN 55672-1:2007-08. The yield was then determined by subtracting the area percentage of the monomer still remaining from the area percentage of the original amount of monomer, which were determined in each case by GPC to DIN 55672-1:2007-08.

| Example | Inventive | | | | | | | Comparative |
|---|---|---|---|---|---|---|---|---|
| Mixture | 1 | 2 | 3 | 4 | 5 | 6 | 7 | 8 |
| Distillation residue from the phosgenation of 1,5-NDA to 1,5-NDI [% by wt.] | 70 | 70 | 85 | 70 | 70 | 70 | 90 | 60 |
| Bitumen 160/220 (2.9% by weight of sulfur) [% by wt.] | 30 | 30 | 15 | — | — | — | 10 | — |
| Bitumen with 3.08% by weight of sulfur [% by wt.] | — | — | — | 30 | — | — | — | — |
| Bitumen with 3.32% by weight of sulfur [% by wt.] | — | — | — | — | — | 30 | — | — |
| Bitumen 70/100 (3.5% by weight of sulfur) [% by wt.] | — | — | — | — | 30 | — | — | 40 |
| Proportion of monomeric 1,5-NDI in the distillation residue [% by wt. based on the distillation residue] | 46.9 | 46.9 | 46.9 | 46.9 | 46.9 | 46.9 | 46.9 | 45.9 |
| Distillation conditions | | | | | | | | |
| Temperature [° C.] | 155 | 155 | 155 | 155 | 155 | 155 | 155 | 160 |
| Pressure [mbar] | 0.9 | 0.9 | 0.9 | 0.9 | 0.9 | 0.9 | 0.9 | 0.9 |
| Dosage rate [g/h] | 230 | 265 | 265 | 265 | 265 | 265 | 265 | 260 |
| Proportion of monomeric 1,5-NDI monomer recovered (yield) [%] | 84.5 | 86.4 | 87.1 | 87.3 | 62.8 | 65.8 | 79.3 | 78.7 |
| Proportion of 1,5-NDI monomer in bottoms output [%] | 7.3 | 8.3 | 6.1 | 6.0 | 17.4 | 17.4 | 9.7 | 9.8 |
| Purity of 1,5-NDI monomer [%] | 99.5 | 99.9 | — | — | — | — | — | 99.7 |

The figures in % by weight for the mixture are based on the mass the overall mixture. The respective mixture was sent to a vacuum distillation in a thin-film evaporator under the conditions specified, with condensation of the monomeric 1,5-NDI in solid form. The bottoms output that was still liquid at this temperature consisted in each case of 1,5-NDI monomer, non-distillable components and bitumen. All examples and comparative examples (except comparative example 9) were conducted in a conventional glass falling-film evaporator with an evaporator area of 0.1 m² (diameter 100 mm, length 300 mm).

Comparative Example 9 (without Thin-Film Evaporator)

Residue from the phosgenation of 1,5-NDA to 1,5-NDI still containing 70-85%1,5-NDI monomer was fed at 150° C. to an amount of bitumen preheated to 160° C. (30% by weight of the residue) in a tank. 1,5-NDI monomer was distilled out of the mixture obtained while stirring continuously at 2-4 mbar and 160° C. The yield of the 1,5-NDI monomer recovered in this method was 50-60%.

Discussion of Results

Comparison of the inventive examples with the comparative examples shows that it is possible by the method of the invention to recover a comparable or even a higher proportion of more than 80% of the monomeric diisocyanate from the distillation residue. Comparative example 8 did achieve a yield of almost 80%, but only by mixing the distillation residue with 40% by weight of bitumen, i.e. consuming more additives.

A further advantage of the method of the invention is that the bottoms output is free-flowing since further oligomerization reactions have been very substantially suppressed by the low temperatures in the performance of the method of the invention compared to conventional methods, which constitutes a significant advantage for the continuous mode of operation. The room temperature solid diisocyanates obtained from the method of the invention are notable for high purity and can be used without restrictions for production of elastomers.

The invention claimed is:

1. A method of separating a room temperature solid diisocyanate from a distillation residue from a method for preparing the diisocyanate, comprising the following steps:
   (i) mixing the distillation residue with a bitumen to obtain a mixture containing 70% to 90% by weight of the distillation residue and 10% to 30% by weight of the bitumen, based in each case on the mixture,
   (ii) distilling the mixture in a thin-film evaporator or a falling-film evaporator to obtain a bottoms output and a gaseous product stream,
   (iii) condensing the gaseous product stream to obtain a solid material comprising the room temperature solid diisocyanate,
   wherein the bitumen in the mixture from step (i) has a sulfur content of 2.5% to 3.1% by weight, based on the bitumen.

2. The method as claimed in claim 1, characterized in that the distillation residue in step (i) contains from 30% to 70% by weight of the room temperature solid diisocyanate, based on the distillation residue.

3. The method as claimed in claim 1, characterized in that, in step (i), 85% to 70% by weight of the distillation residue is mixed with from 15% to 30% by weight of the bitumen, based in each case on the sum total of the masses of the distillation residue and the bitumen.

4. The method as claimed in claim 1, characterized in that step (ii) is performed at a temperature of 130° C. to 160° C. and a pressure of 0.4 to 4 mbar.

5. The method as claimed in claim 1, characterized in that the bottoms output from step (ii) is not in solid form at the prevailing temperature at the outlet from the thin-film evaporator or falling-film evaporator.

6. The method as claimed in claim 1, characterized in that the solid material from step (iii) contains at least 95% by weight of the room temperature solid diisocyanate, based on the solid material.

7. The method as claimed in claim 1, characterized in that the method for preparing the diisocyanate is a phosgenation of a diamine.

8. The method as claimed in claim 1, characterized in that the room temperature solid diisocyanate is naphthalene 1,5-diisocyanate, naphthalene 1,8-diisocyanate, phenylene 1,4-diisocyanate, tetralin diisocyanate, o-toluidine diisocyanate, durene diisocyanate, benzidine diisocyanate and/or anthrylene 1,4-diisocyanate.

\* \* \* \* \*